United States Patent
Rodgers et al.

(10) Patent No.: US 7,588,670 B2
(45) Date of Patent: Sep. 15, 2009

(54) ENZYMATIC ELECTROCHEMICAL-BASED SENSOR

(75) Inventors: James Iain Rodgers, Inverness (GB); Zuifang Liu, Inverness (GB); Alan Watson McNeilage, Inverness (GB); Margaret MacLennan, Culloden (GB); James Moffat, Inverness (GB); Geoffrey Lillie, Inverness (GB); Michael MacDonald, Inverness (GB)

(73) Assignee: LifeScan Scotland Limited (GB)

( * ) Notice: Subject to any disclaimer, the term of this patent is extended or adjusted under 35 U.S.C. 154(b) by 167 days.

(21) Appl. No.: 11/118,507

(22) Filed: Apr. 28, 2005

(65) Prior Publication Data
US 2006/0226006 A1  Oct. 12, 2006

Related U.S. Application Data

(60) Provisional application No. 60/671,026, filed on Apr. 12, 2005.

(51) Int. Cl.
*G01N 27/327* (2006.01)

(52) U.S. Cl. .............. 204/403.14; 204/403.04

(58) Field of Classification Search .......... 204/403.01–403.15; 205/777.5, 778, 792
See application file for complete search history.

(56) References Cited

U.S. PATENT DOCUMENTS

| | | |
|---|---|---|
| 3,349,055 A | 10/1967 | Akira |
| 4,226,938 A | 10/1980 | Yoshida et al. |
| 4,874,549 A | 10/1989 | Michalchik |
| 5,089,112 A | 2/1992 | Skotheim et al. |
| 5,707,502 A | 1/1998 | McCaffrey et al. |
| 5,820,551 A | 10/1998 | Hill et al. |
| 6,134,461 A | 10/2000 | Say et al. |
| 6,284,478 B1 | 9/2001 | Heller et al. |
| 6,599,408 B1 | 7/2003 | Chan et al. |
| 6,627,058 B1 | 9/2003 | Chan |
| 6,736,957 B1 | 5/2004 | Forrow et al. |
| 6,764,581 B1 | 7/2004 | Forrow et al. |
| 2003/0151028 A1 | 8/2003 | Lawrence et al. |
| 2006/0025550 A1 | 2/2006 | Liu et al. |
| 2006/0042944 A1 | 3/2006 | Rodgers et al. |
| 2006/0069211 A1 | 3/2006 | Liu et al. |

FOREIGN PATENT DOCUMENTS

| | | |
|---|---|---|
| EP | 0352925 A | 1/1990 |
| EP | 0755695 B1 | 1/1997 |
| EP | 0757246 A | 2/1997 |
| EP | 0992589 A | 4/2000 |
| JP | 07 270374 A | 10/1995 |
| WO | WO 03/054070 A2 | 7/2003 |

OTHER PUBLICATIONS

European Partial Search Report dated Jul. 28, 2006, for EP Appl. No. 06252010.1.
A. Heller, et al. Electrical Wiring of redox Enzymes, Acc. Chem. Res. (1990) vol. 23, pp. 128-134.

(Continued)

*Primary Examiner*—Alex Noguerola

(57) ABSTRACT

An enzymatic electrochemical-based sensor includes a substrate and a conductive layer formed from a dried water-miscible conductive ink. The water-miscible conductive ink used to form the conductive layer includes a conductive material, an enzyme, a mediator, and a binding agent and is formulated such that the water-miscible conductive ink is a water-miscible aqueous-based dispersion and the binding agent became operatively water-insoluble upon drying.

9 Claims, 13 Drawing Sheets

OTHER PUBLICATIONS

P.D. Hale, et al. Amperometric glucose biosensors based on redox polymer-mediated electron transfer, Anal. Chem. (1991) vol. 63 677-682.

L. Boguslavsky, et al. Thin film bienzyme amperometric biosensors based on polymeric redox mediators with electrostatic bipolar protecting layer, Analytical Chimica acta. (1995) vol. 311, pp. 15-21.

Sartomer Application Bullentin, A New pH Neutral Waterborne Dispersing Resin For Metallic And Organic Pigments, Sartomer Company, Jul. 2001.

Takahiro Saito, et al., "Characterization of poly(vinylferrocene-co-2-hydroxyethyl methacrylate) for use as electron mediator in enzymatic glucose sensor", Reactive & Functional Polymers, vol. 37 (1998) 263-269.

Patent Abstracts of Japan Publication No. 10-113200, "Enzyme Electrode" dated Jun. 5, 1998, Iatron Lab Inc.

J. Gun, et al., "Sol-gel derived, ferrocenyl-modified silicate-graphite composite electrode: Wiring of glucose oxodase" Analytica Chimica Acta 336 (1996) 95-106, Jerusalem, Israel.

ENZYMATIC ELECTROCHEMICAL-BASED SENSOR

CROSS-REFERENCE

This application claims the benefit of U.S. Provisional Application No. 60/671,026, filed Apr. 12, 2005.

BACKGROUND OF THE INVENTION

1. Field of the Invention

The present invention relates, in general, to sensors and, in particular, to enzymatic electrochemical-based sensors.

2. Description of the Related Art

The use of enzymatic electrochemical-based sensors that employ an enzymatic reagent, for example, an enzymatic reagent that includes a redox mediator (e.g., ferrocene) and a redox enzyme (e.g., glucose oxidase), in conjunction with an electrode(s) for the determination of an analyte in a liquid sample has become of heightened interest in recent years. Such enzymatic electrochemical-based sensors are believed to be particularly suitable for continuous or semi-continuous monitoring of analytes (e.g., glucose) in a fluid samples (e.g., blood or interstitial fluid samples). For example, enzymatic electrochemical-based glucose sensors employing a redox mediator, a redox enzyme and a working electrode can determine (i.e., measure) glucose concentration using relatively low potentials (e.g., less than 0.4 V vs SCE), thereby limiting any interfering responses, at the working electrode. For a further description of enzymatic electrochemical-based sensors, see, for example, U.S. Pat. Nos. 5,089,112 and 6,284,478, each of which is hereby fully incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which.

DETAILED DESCRIPTION OF ILLUSTRATIVE EMBODIMENTS OF THE INVENTION

Figure 1:
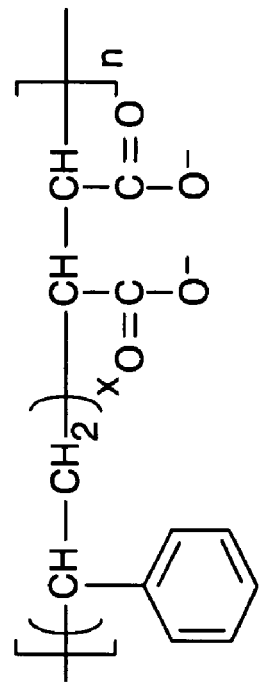
FIG. 1 depicts a copolymer that can be employed in a binding agent of a water-miscible conductive ink according to an exemplary embodiment of the present invention.
Figure 2:
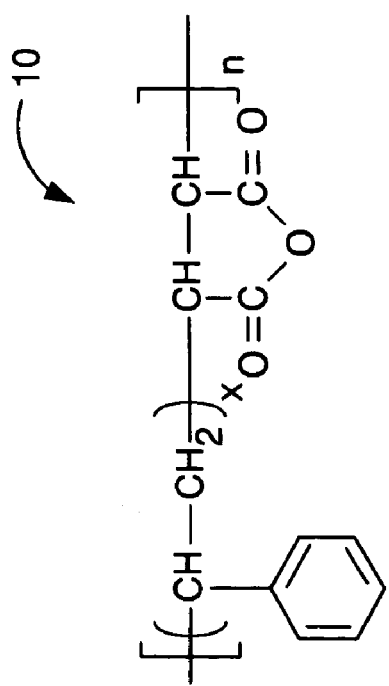
FIG. 2 depicts another copolymer that can be employed in a binding agent of a water-miscible conductive ink according to another exemplary embodiment of the present invention.

A water-miscible conductive ink for use in an enzymatic electrochemical-based sensor according to an embodiment of the present invention includes a conductive material, an enzyme, a mediator and a binding agent. In addition, the conductive material, enzyme, mediator and binding agent are formulated as a water-miscible aqueous-based dispersion wherein the binding agent becomes operatively water-insoluble upon drying. In this regard, one skilled in the art will recognize that a dispersion is essentially a mixture comprising discrete particle material (e.g., particles of conductive material) dispersed in a continuous phase of a different material (e.g., a continuous binding agent phase). Characteristics, benefits and other exemplary details of water-miscible conductive inks for use in an enzymatic electrochemical-based sensor according to various exemplary embodiments of the present invention are described below.

Water-miscible conductive inks according to embodiments of the present invention enable close proximal juxtaposition between the enzyme, the mediator, and the conductive material, thereby facilitating rapid electron exchange (i.e., electron transfer) therebetween. Such rapid electron exchange can lead to a beneficial increase in current collection efficiency.

Water-miscible conductive inks according to embodiments of the present invention are readily employed in conventional enzymatic electrochemical-based sensor manufacturing techniques such as, for example, screen printing techniques. Furthermore, embodiments of the water-miscible conductive ink are suitable for being immobilized upon drying to a substrate of an enzymatic electrochemical-based sensor as a conductive layer, thus preventing loss of mediator and/or enzyme from the conductive layer during use of the enzymatic electrochemical-based sensor. In addition, in comparison to a conventional discrete electrode, the conductive material of such a conductive layer can have a greater mediator accessible surface area.

Since water-miscible conductive inks according to embodiments of the present invention are formulated as aqueous-based dispersions, they are readily compatible with typical enzymes and mediators. In addition, water-miscible conductive inks according to embodiments of the present invention are advantageous in that their water-miscible nature enables a wide formulation latitude in terms of the proportion of enzyme and mediator which can be incorporated therein as a uniform dispersion.

Water-miscible conductive inks according to embodiments of the present invention can be easily manufactured, and are readily applied to substrates of an enzymatic electrochemical-based sensor. The water-miscible conductive inks are, therefore, beneficially suitable for rapid and cost effective production of enzymatic electrochemical-based sensors. Furthermore, since embodiments of water-miscible conductive inks according to embodiments of the present invention combine an enzyme, mediator and a conductive material into a single composition, the number of processing steps and expense required to manufacture an enzymatic electrochemical-based sensor is beneficially reduced.

It should be noted that a water-miscible conductive ink according to embodiments of the present invention is a conductive ink that can be dissolved and/or otherwise dispersed uniformly in water or other aqueous solution, although the water-miscible conductive ink can also include an organic solvent that does not induce phase separation (i.e., a water-miscible organic solvent).

Suitable conductive materials, enzymes, mediators and binding agents, as well as a descriptions of suitable techniques for formulating the conductive materials, enzymes, mediators and binding agents into a water-miscible conductive ink according to embodiments of the present invention are detailed below.

Conductive Material

Any suitable conductive material (also referred to as a pigment or carbon ink as a context may warrant) known to one skilled in the art can be employed in embodiments of the present invention. For example, the conductive material can be a finely divided conductive particle material such as a carbon black material, graphite material, a platinum particle material, a platinized carbon material, a gold particle material, a platinum/palladium alloy particle material, a palladium particle material, a ruthenium, particle material, or a cerium particle material. The size of such finely divided conductive particle material can be, for example, less than 100 microns and, preferably, in the size range of 1 nm to 20 microns. In addition, the size range can have a bimodal distribution.

When a water-miscible conductive ink according to embodiments of the present invention is employed to manufacture a conductive layer of an enzymatic electrochemical-based sensor, the conductive material of the water-miscible conductive ink can serve as an electrode and exchange electrons with the mediator of the water-miscible conductive ink. In this regard, once apprised of the present disclosure, one skilled in the art will recognize that conductive layers formed from water-miscible conductive inks according to the present invention contain the conductive material, enzyme and mediator that were present in the water-miscible conductive ink used to form the conductive layer. Since the conductive material and the mediator (as well as the enzyme and binding agent) can be formulated as a uniform dispersion, the resulting conductive layer has an enhanced ability for electron exchange between the conductive material and the mediator in comparison to electron exchange between a discrete conductive material layer (such as a conventional electrode) and a separate mediator-containing layer.

Once apprised of the present disclosure, one skilled in the art can select a combination of conductive particles, binding agent, mediator, enzyme, and, optionally, a water-miscible organic co-solvent that produce a uniform dispersion and, upon drying, a uniform conductive layer (e.g., a conductive layer with an essentially uniformly distributed enzyme, mediator and conductive material). Conventional and well-known experimental techniques for assessing uniformity of dispersions and conductive layers (such as visual and Scanning Electron Microscopy (SEM) inspection and mechanical characterization) can be employed in doing so.

The electrical characteristics of conductive material (as well as the binding agent) employed in a water-miscible conductive ink, and the proportion of the conductive material, can be predetermined such that a conductive layer formed by drying the water-miscible conductive ink has a conductivity of less than about 10 k$\Omega$. In this regard, it can be particularly beneficial to form a conductive layer with a conductivity of less than about 1 k$\Omega$.

Enzyme

Any suitable enzyme known to one skilled in the art can be employed in embodiments of the present invention. The enzyme can be, for example, an enzyme that selectively recognizes an analyte (e.g., glucose) to be determined (i.e., detected or measured) within a fluid sample (such as a blood sample). As is known to one skilled in the art of enzymatic electrochemical-based sensors, such an enzyme partakes in an electrochemical reaction that is the basis for an electrochemical determination of the analyte by an enzymatic electrochemical-based sensor. For example, the enzyme may shuttle electrons to an electrode (or other conductive material) using a mediator, thereby enabling a current to be measured at the electrode which is proportional to analyte concentration.

The enzyme can be, for example, a redox enzyme such as a glucose oxidizing enzyme. In this circumstance, an enzymatic electrochemical-based sensor that employs a water-miscible conductive ink containing a glucose oxidizing enzyme can be used to determine glucose in a fluid sample (e.g., a whole blood sample). Examples of a glucose oxidizing enzymes include, but are not limited to, glucose oxidase and pyrrolo-quinoline-quinone (PQQ) glucose dehydrogenase.

The formulations of water-miscible conductive inks according to embodiments of the present invention enable the enzyme of such water-miscible conductive inks to be operatively immobilized to a substrate of an enzymatic electrochemical-based sensor. The operative immobilization is such that the enzyme, while immobilized to the substrate, is able to react with an analyte and transfer electrons to the conductive material via the mediator.

Mediator

Any suitable mediator known to one skilled in the art can be employed in embodiments of the present invention. A mediator is essentially a chemical entity that can operatively exchange electrons with both the conductive material and the enzyme of the water-miscible conductive ink.

The mediator can be, for example, ferricyanide or ferrocene. In addition, the mediator can be a polymeric mediator such as those described, and referred to as redox polymers, in co-pending U.S. patent application Ser. No. 10/957,441, application Ser. No. 10/931,724, and application Ser. No. 10/900,511. Such polymeric mediators can be water soluble and of a high molecular weight, such as a co-polymer of vinyl ferrocene and acrylamide.

A suitable mediator with limited water-solubility such as, for example, ferrocene or tetrathiafulvalene/tetracyanoquinodomethane (TTF/TCNQ) can be prepared for formulation into a water-miscible conductive ink according to embodiments of the present invention by dispersion or dissolution of the mediator into a water miscible co-solvent such as, for example, methyl carbitol or a glycol ether solvents prior to formulation. Such a water-miscible co-solvent enables the mediator to be effectively dispersed with the conductive material, enzyme and binding agent of the water-soluble conductive ink despite the limited water-solubility of the mediator in the absence of the co-solvent.

The formulations of water-miscible conductive inks according to embodiments of the present invention enable the mediator to be operatively immobilized to a substrate of an enzymatic electrochemical-based sensor. The operative immobilization is such that the mediator, while immobilized to the substrate, is able to react with an enzyme and transfer electrons to the conductive material.

Binding Agent

Any suitable binding agent (also referred to as a resin or resin polymer as a context may warrant) known to one skilled in the art can be employed in embodiments of the present invention. This binding agent of water-miscible conductive inks according to embodiments of the present invention serves to operatively immobilize the conductive material, mediator and enzyme of the water-miscible conductive ink to a substrate of an enzymatic electrochemical-based sensor.

The binding agent can include, for example, a resin polymer and a counter-ion, wherein the counter-ion renders the resin polymer soluble in water by deprotonating or protonating an acid or base group of the resin polymer. The counter-ion can be volatile, such that when the water-miscible conductive ink is dried, the counter ion essentially evaporates and the resulting binding agent (i.e., the dried resin polymer) becomes operatively water insoluble. For example, the resin polymer can have an acid group derived from a carboxylic acid species, and the volatile counter ion can be derived from a volatile amine such as ammonia, N'N'dimethylethanolamine, or a volatile organic amine. When the volatile counter-ion evaporates from the water-soluble conductive ink, the resin polymer can become ionically cross-linked onto a substrate of an enzymatic electrochemical-based sensor in such a way that the enzyme, conductive material, and mediator of the water-insoluble conductive ink are substantially immobilized. For a resin polymer with negatively-charged acid groups, the negatively charged acid groups may ionically bind with positively charged species on the resin polymer itself or with any of the conductive material, the enzyme and the mediator.

Alternatively, for example, an acid or base groups of a polymeric resin can be such that the acid or base group is only ionized within a predetermined pH range, thus rendering the polymeric resin water soluble within the predetermined pH range. Upon drying of the water-miscible conductive ink, the dried or drying ink can be treated with a solution of an appropriate pH beyond the predetermined pH range to render the polymeric resin operatively water insoluble.

The usefulness of binding agents can be enhanced by the action of co-solvency effects, whereby the presence of a water miscible organic co-solvent in the water-miscible conductive ink improves the water-solubility of the binding agent. Such organic co-solvents can be, for example, removed by evaporation when the water-miscible conductive ink is dried. Notably, upon contact with a fluid sample during use of the enzymatic electrochemical-based sensor, the organic solvent is absent and the resin polymer is operatively water-insoluble. Suitable water miscible organic co-solvents include, for example, alcohols, glycol ethers, methyl carbitol, butyl carbitol, ethylene glycol, ethylene glycol diacetate, diacetone alcohol and triethyl phosphate.

Once apprised of the present disclosure, one skilled in the art will recognize that various components of water-miscible conductive inks according to the present invention are commercially available. For example, a water-miscible combination of conductive graphite material and binding agent suitable for use in various embodiments of water-miscible conductive inks according to the present invention is available as a conductive graphite paste from Coates Electrographics, a division of Sun Chemical Screen, Norton Hill, Midsomer Norton, Bath UK, under the catalog number 66756. A further water-miscible combination of conductive material and binding agent is commercially available from Precisia, Ann Arbor, Mich., U.S.A. as water-soluble conductive material LFW201-H The dried binding agent of a conductive layer formed by drying various embodiments of water-miscible conductive inks according to the present invention can serve as a dialytic membrane, with the mediator, enzyme, and conductive material being constrained within the dried and operatively water insoluble binding agent and, thereby, immobilized to a substrate of an enzymatic electrochemical-based sensor. Such a dialytic membrane can allow relatively small molecules, such as glucose, to penetrate therein and interact with the constrained enzyme.

Figure 3:
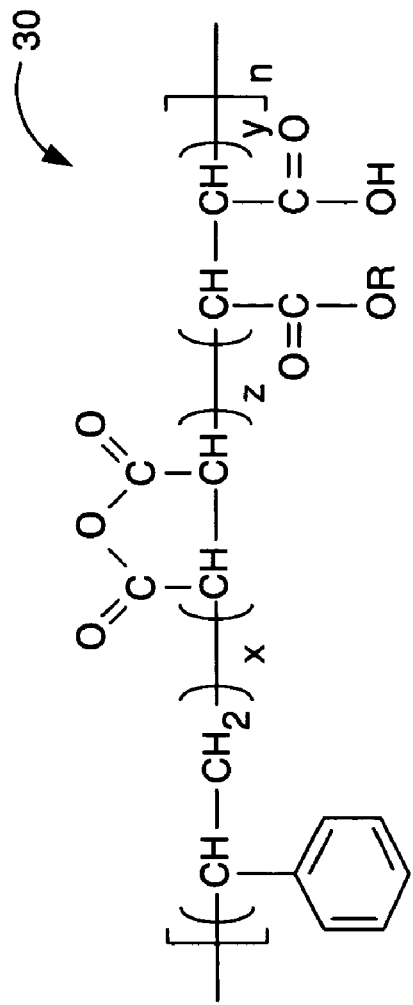
FIG. 3 depicts yet another copolymer that can be employed in a binding agent of a water-miscible conductive ink according to yet another exemplary embodiment of the present invention.
Figure 4:
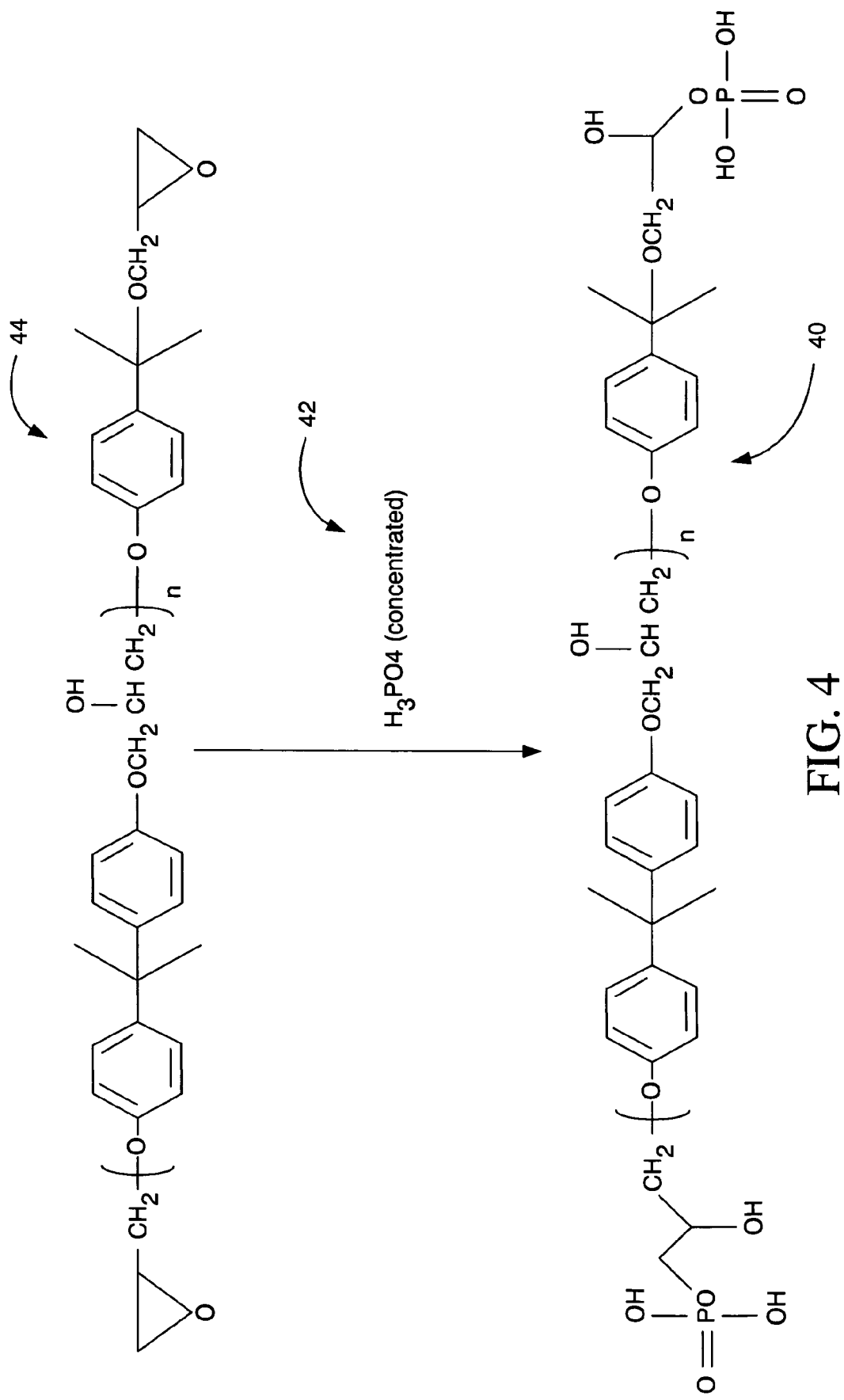
FIG. 4 depicts a reaction sequence for creating a copolymer that can be employed in a binding agent of a water-miscible conductive ink according to a further exemplary embodiment of the present invention.

Referring to FIGS. 1, 2, 3 and 4, suitable binding agents for use in water-miscible conductive inks according to embodiments of the present invention can include a polymer with carboxylic functional groups, anhydride functional groups, and/or phosphoric acid groups. For example, the binding agent may be a copolymer of polystyene-co-maleic anhydride 10 depicted in FIG. 1, a hydrolyzed copolymer of polystyene-co-maleic anhydride 20 depicted in FIG. 2, a copolymer of polystyene-co-maleic anhydride which is partially hydrolyzed, a partially esterified copolymer of polystyene-co-maleic anhydride 30 as depicted in FIG. 3, or a phosphoric acid functional polymer 40 derived by the reaction of phosphoric acid 42 with epoxy resin 44 as depicted in FIG. 4.

Furthermore, binding agents can also be formulated to contain a copolymer or terpolymer made by blending suitable acid functional vinyl monomers, such as an acrylic acid monomer, and/or a methacrylic acid monomer, and/or an itaconic acid monomer, and/or a maleic acid monomer, along with other vinyl monomers, such as a methyl methacrylate monomer, and/or a styrene monomer, and/or an ethyl acrylate monomer, and/or an isopropyl acrylate monomer, and/or a butyl acrylate monomer, and/or an acrylonitrile monomer, and/or a methyl styrene monomer, and/or a vinyl benzoate monomer, and/or an acrylamide monomer, and/or and a hydroxymethyl methacrylate monomer. Such polymeric binding agents combine water miscibility with excellent conductive material dispersant properties.

Referring to FIGS. 5A, 5B, 5C and 5D, an enzymatic electrochemical-based sensor 100 according to an embodiment of the present invention includes a substrate 102, a reference electrode 104a with an electrode surface 106a, a working electrode 104b with an electrode surface 106b, and a conductive layer 108 disposed on electrode surface 106b. Conductive layer 108 is formed by drying a water-miscible conductive ink according to embodiments of the present invention as described herein. Therefore, conductive layer 108 includes a dried binding agent (that is operatively water insoluble), a mediator, an enzyme and conductive material. Although conductive layer 108 is depicted as being disposed on working electrode 104b, a conductive layer formed from water-miscible conductive inks according to embodiments of the present invention can themselves serve as a working electrode or other suitable conductive component of an enzymatic electrochemical-based sensor.

Enzymatic electrochemical-based sensor 100 also includes a reference ink layer 114 and an optional insulation layer 112. One skilled in the art will recognize that FIGS. 5A through 5D depict only a portion of a complete enzymatic electrochemical-based sensor and that additional components of the enzymatic electrochemical-based sensor (e.g., a housing, analysis/microprocessor module, and electrical communication circuits) have not been illustrated to avoid unduly complicating FIGS. 5A through 5D.

One skilled in the art will also recognize that reference ink layer 114, which constitutes an electrochemically active layer integrated with reference electrode 104a, sets the "zero potential" against which a measurement potential is applied at working electrode 104b. One skilled in the art will further recognize that although FIGS. 5A through 5D depict an enzymatic electrochemical-based sensor with a two electrode format, other enzymatic electrochemical-based sensor formats known in the field can be employed in embodiments of the present invention.

Substrate 102 can be formed, for example, from a sheet of polyethylene terephthallate, polybutylene terephthallate sheet (commercially available from, for example, GE Plastic, United States), or from an oriented polystyrene film (commercially available from, for example, NSW GmBH, Germany).

Reference ink layer 114 can be formed, for example, from Ag/AgCl paste (commercially available from Gwent Electronic Materials, Pontypool Wales, UK) or any suitable electrochemical reference material including, but not limited to materials that include a metal that forms a partially soluble salt (e.g., silver, copper, titanium and lithium).

The optional insulation layer 112 can be formed, for example, from a dielectric screen printable ink paste (commercially available from, for example, Sericol Inks Ltd.). Reference electrode 104a and working electrode 104b can be formed of any suitable material known to one skilled in the art.

Reference electrode 104a, working electrode 104b, insulation layer 112 can have any suitable thickness. However, a typical thickness for each of these layers is in the range of from 1 micron to 100 microns.

Figure 5A:
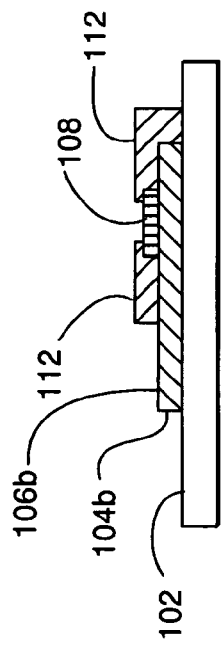
FIG. 5A is a simplified top view depiction of a portion of an enzymatic electrochemical-based sensor according to an exemplary embodiment of the present invention.
Figure 5B:
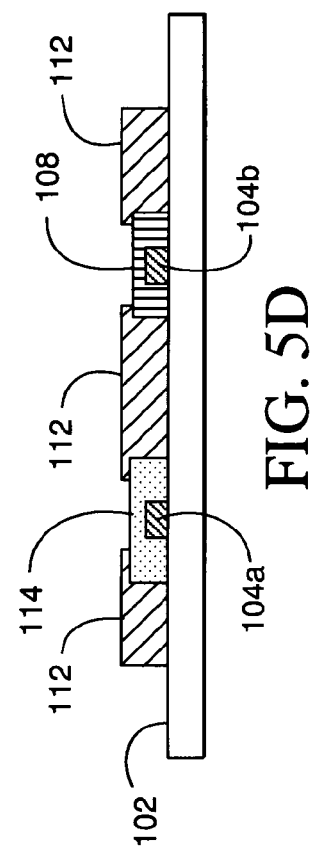
FIG. 5B is a simplified cross-sectional depiction of the enzymatic electrochemical-based sensor of FIG. 5A taken along line 5B-5B.
Figure 5C:
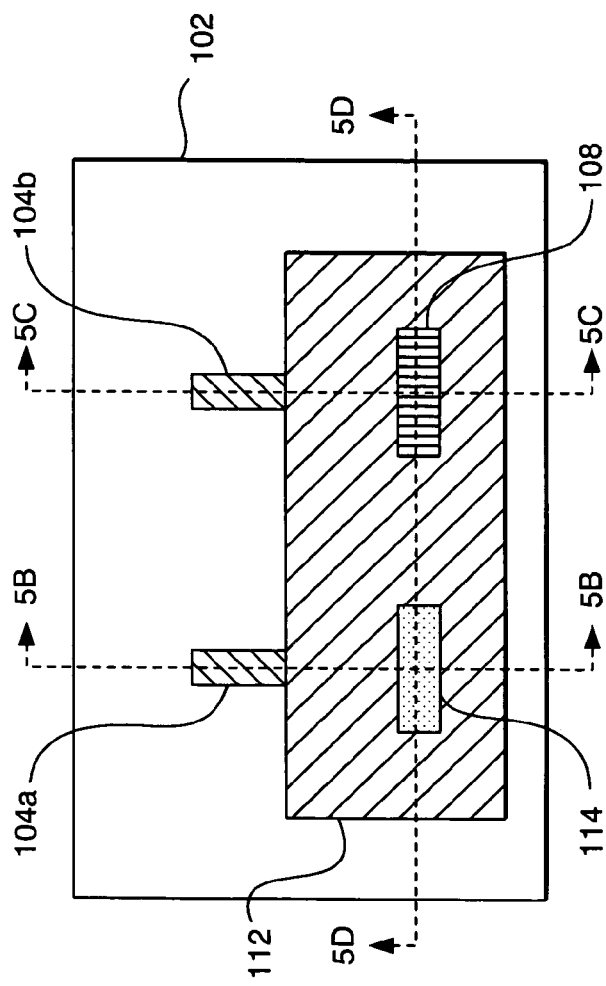
FIG. 5C is a simplified cross-sectional depiction of the enzymatic electrochemical-based sensor of FIG. 5A taken along line 5C-5C.
Figure 5D:
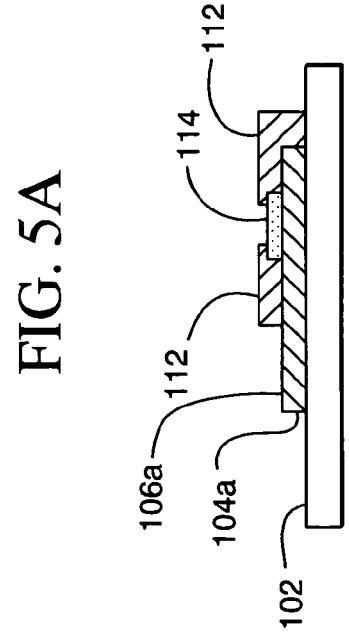
FIG. 5D is a simplified cross-sectional depiction of the enzymatic electrochemical-based sensor of FIG. 5A taken along line 5D-5D.
Figure 6:
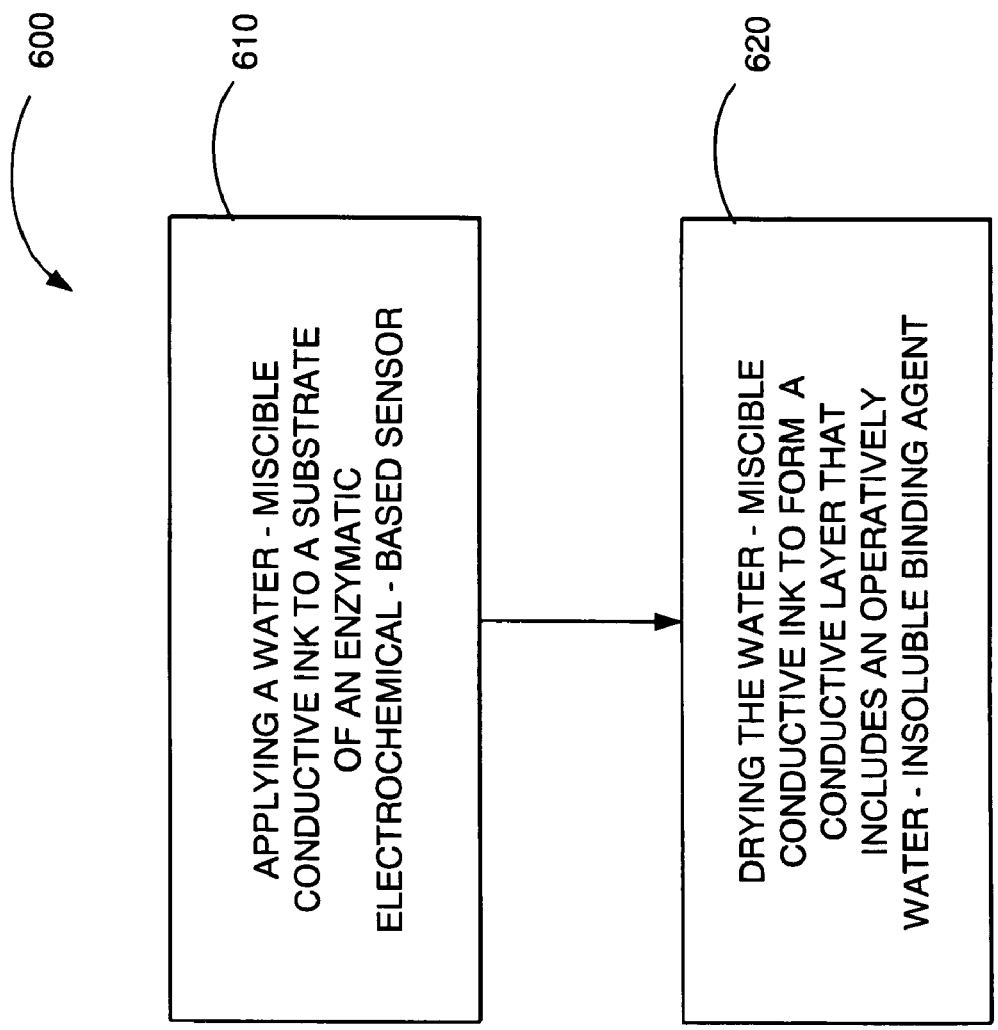
FIG. 6 is a flow chart of a process for manufacturing a portion of an enzymatic electrochemical-based sensor according to an exemplary embodiment of the present invention.

FIG. 6 is a flow chart of a method 600 for manufacturing an enzymatic electrochemical-based sensor according to an exemplary embodiment of the present invention. The manufactured portion can be any conductive layer such as, for example, an electrode, an electrically conductive trace or the conductive layer depicted in FIGS. 5A through 5D. However, one skilled in the art will recognize that although FIGS. 5A through 5D illustrate an enzymatic electrochemical-based sensor that can be manufactured using methods according to the present invention, the methods are not limited to the enzymatic electrochemical-based sensor depicted in FIGS. 5A through 5D.

Method 600 includes applying a water-miscible conductive ink to a substrate of an enzymatic electrochemical-based sensor, as set forth in step 610. The water-miscible conductive ink includes a conductive material, an enzyme, a mediator, and a binding agent, with the conductive material, enzyme, mediator, and binding agent formulated as a water-miscible aqueous-based dispersion and wherein the binding agent becomes operatively water-insoluble upon drying.

The substrate can be any suitable substrate including, for example, an electrically insulating substrate of an enzymatic electrochemical-based sensor and/or a conducting substrate of an enzymatic electro-chemical based sensor.

The application of step 610 can be accomplished using, for example, any suitable application technique including screen printing techniques, dip coating techniques, spray coating techniques, and inkjet coating techniques. The water-miscible conductive ink applied in step 610 is further described herein with respect to water-miscible conductive inks and enzymatic electrochemical-based sensors according to the present invention.

As illustrated in step 620 of FIG. 6, method 600 further includes drying the water-miscible conductive ink to form a conductive layer on the substrate that includes an operatively water-insoluble binding agent.

The drying can be conducted at a temperature and for a time period that is sufficient to immobilize the dried water-soluble conductive ink to the substrate and form the conductive layer, but insufficient to significantly degrade the activity of the enzyme. For example, the water-miscible conductive ink can be dried at about 75° C. for about 20 minutes.

EXAMPLE 1

A water-miscible conductive ink according to an exemplary embodiment of the present invention that included the enzyme glucose oxidase, the mediator ferrocene and a commercially available combination of conductive material and binding agent (available from Coates as water-miscible graphite paste 66756) was prepared. The water-miscible conductive ink was formulated as follows: 50 mg of glucose oxidase was dissolved in 0.7 ml of Analar water. The resulting solution was added to 5 g of water-miscible graphite paste 66756, followed by mixing with 25 mg of ferrocene that had been dissolved in 1 ml of methyl carbitol co-solvent.

A portion of the water-miscible conductive ink described above was coated onto a glassy carbon electrode and dried in an oven at 75° C. for 20 minutes to create a glassy carbon electrode with a conductive layer thereon. One skilled in the art will recognize that such an electrode with a conductive layer thereon represents a portion of an enzymatic electrochemical-based sensor.

The electrode with the conductive layer thereon was tested at a constant potential of 300 mV in a beaker containing a stirred buffered glucose solution. The test employed a silver/silver chloride reference electrode and a platinum wire counter electrode. An amperometric response to increasing glucose concentration in the beaker was observed. Amperometric testing was performed for a period in excess of 12 hours, through successive changes in buffer and glucose additions. Upon extended testing, the amperometric response decreased. It is postulated that the decrease was a result of a loss of mediator from the conductive layer.

EXAMPLE 2

Figure 7:
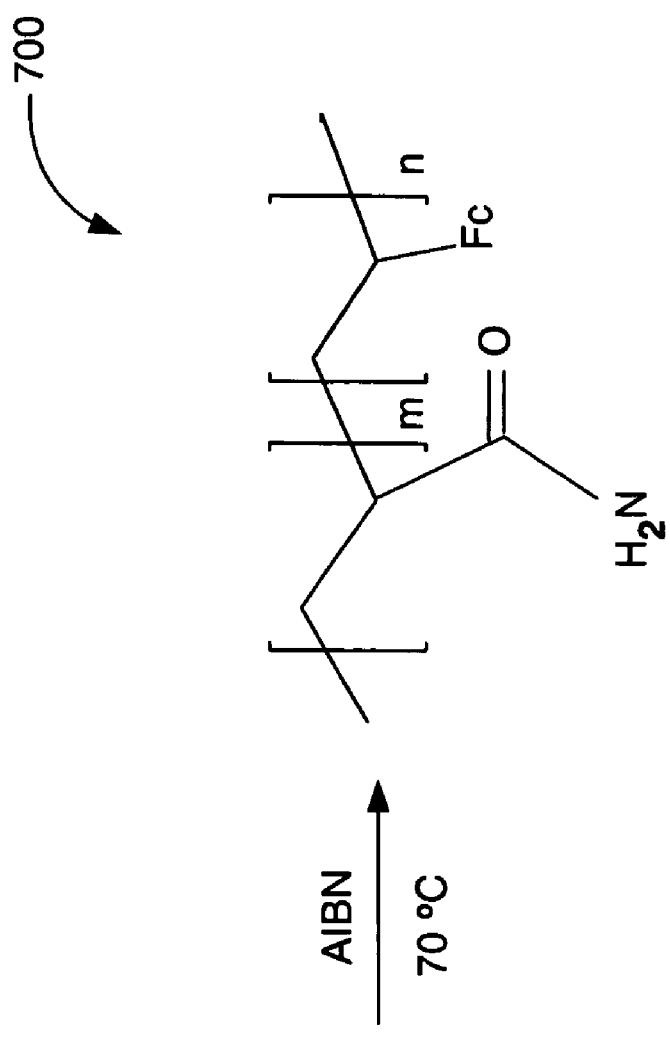
FIG. 7 depicts a simplified reaction sequence for the synthesis of a high molecular weight redox copolymer of acrylamide and vinylferrocene that can be employed in a binding agent of a water-miscible conductive ink according to an exemplary embodiment of the present invention.
Figure 7:
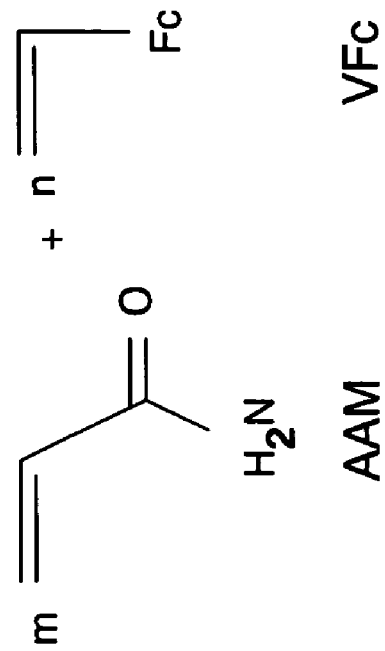

A hydrophilic high molecular weight redox polymer (i.e., redox polymer 700 of FIG. 7) suitable for use in a water-miscible conductive ink according to an embodiment of the present invention was synthesized by the free radical co-polymerization reaction depicted in FIG. 7 using a reaction solution of 1.8 g of 97% acrylamide (AAM), 0.3 g of 97% vinylferrocene (VFc), and 0.03 g of 2.2'-azobisisobutyronitrile (AIBN) in a 40 mL mixture of dioxane and ethanol (1/1 v/v). The reaction was performed in a round bottom flask. The reactions was performed with 5 molar percent of vinyl ferrocene and a 95 molar percent of acrylamide.

Before initiating the reaction, the reaction solution described above was deoxygenated by bubbling nitrogen therethrough for one hour. The reaction solution was then heated to 70° C. in an oil bath for 24 hours with continuous magnetic agitation under a nitrogen atmosphere. The resulting polymer precipitate was filtered off and repeatedly washed with acetone to provide a purified sample of polymer precipitate. The purified sample was subsequently dried in an oven at 50° C.

Relatively low molecular weight portions were then eliminated from the dried purified sample through dialysis against de-ionized water using a cellulose membrane tubing with a molecular weight cutoff of 13 Kg/mol. The resulting composition was a hydrophilic high molecular weight redox polymer (i.e., redox polymer 700 of FIG. 7).

EXAMPLE 3

A water-miscible conductive ink in accordance with an embodiment of the present invention was formulated using redox polymer 700 described in Example 2. The formulation included mixing together 30 mg of glucose oxidase (obtained from *Aspergillus Niger*), 160 mg of a 5% aqueous solution of redox polymer 700, 1 ml of Analar water, 3 g of water miscible graphite paste (commercially available from Coates Screen, a division of Sun Chemical, as catalog number 66756) to form a homogeneous aqueous-based dispersion.

The water-miscible conductive ink described immediately above was coated onto a substrate of an enzymatic electrochemical-based sensor (namely, sensor artwork of 3.75 square millimeters with conductive tracks and a reference (screen printed Ag/AgCl) electrode). The coated substrate was dried at 75° C. for 20 minutes. The dried coated substrate was then placed into a flow-through cell, and connected to a potentiostat. A potential of 300 mV was applied to a working electrode (formed from the water-miscible conductive ink as described immediately above), with a Pt wire inserted into the cell to act as a counter electrode).

Phosphate buffered saline (PBS) containing glucose at physiologically relevant concentrations in the range of 0-20 mmol/L was flowed across the enzymatic electrochemical-based sensor at 0.7 ml/minute. The generated current response was proportional to the glucose concentration of the analyte being flowed at a given point in time, as exemplified by the data of FIG. 8A, and was stable for a period in excess of 20 hours. The stability is further exemplified by the data of FIG. 8B, which depicts 11 hours of data.

Figure 8A:
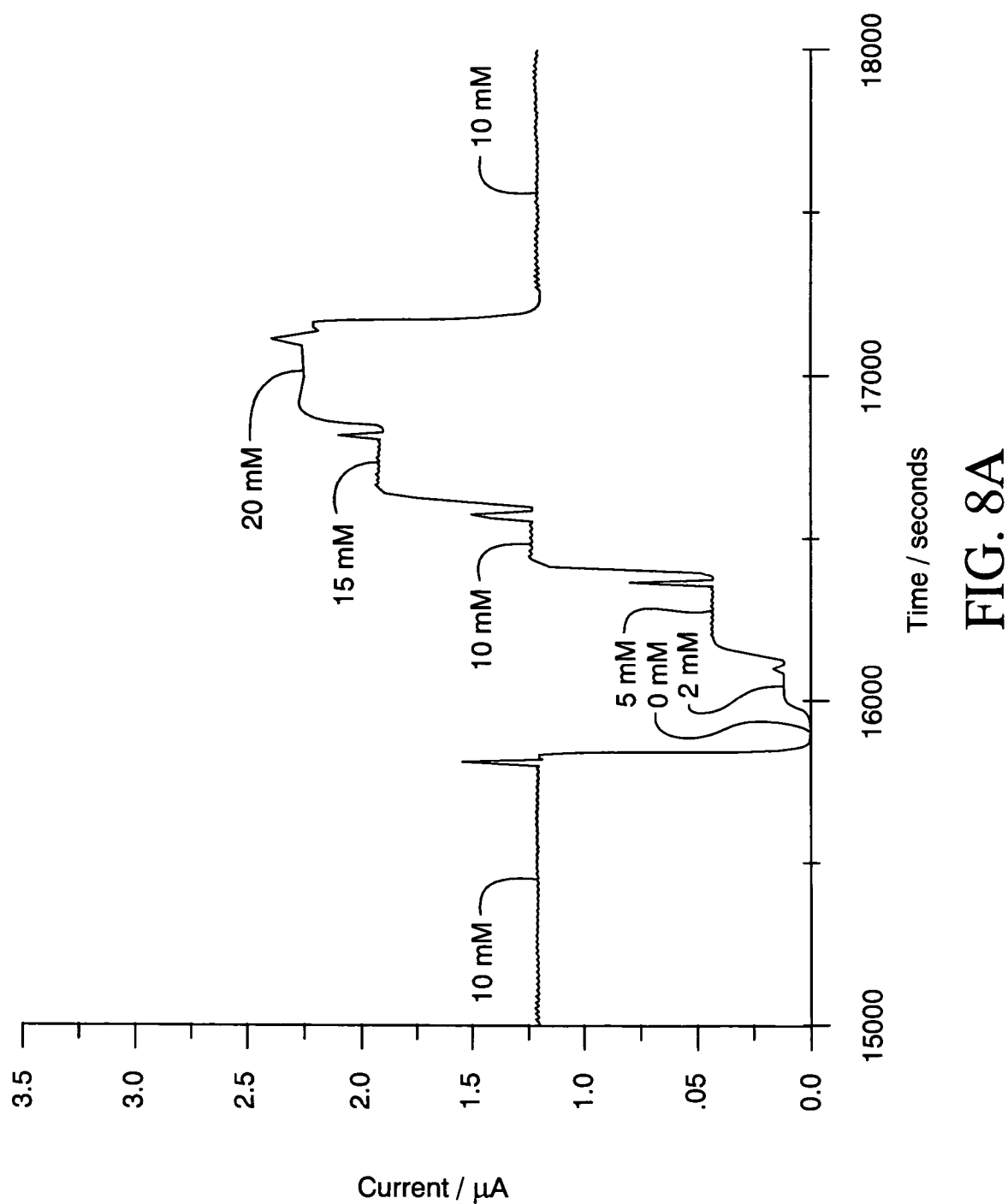
FIG. 8A is a graph depicting calibration data of an enzymatic electrochemical-based glucose sensor according to an exemplary embodiment of the present invention obtained in a continuous flow mode.
Figure 8B:
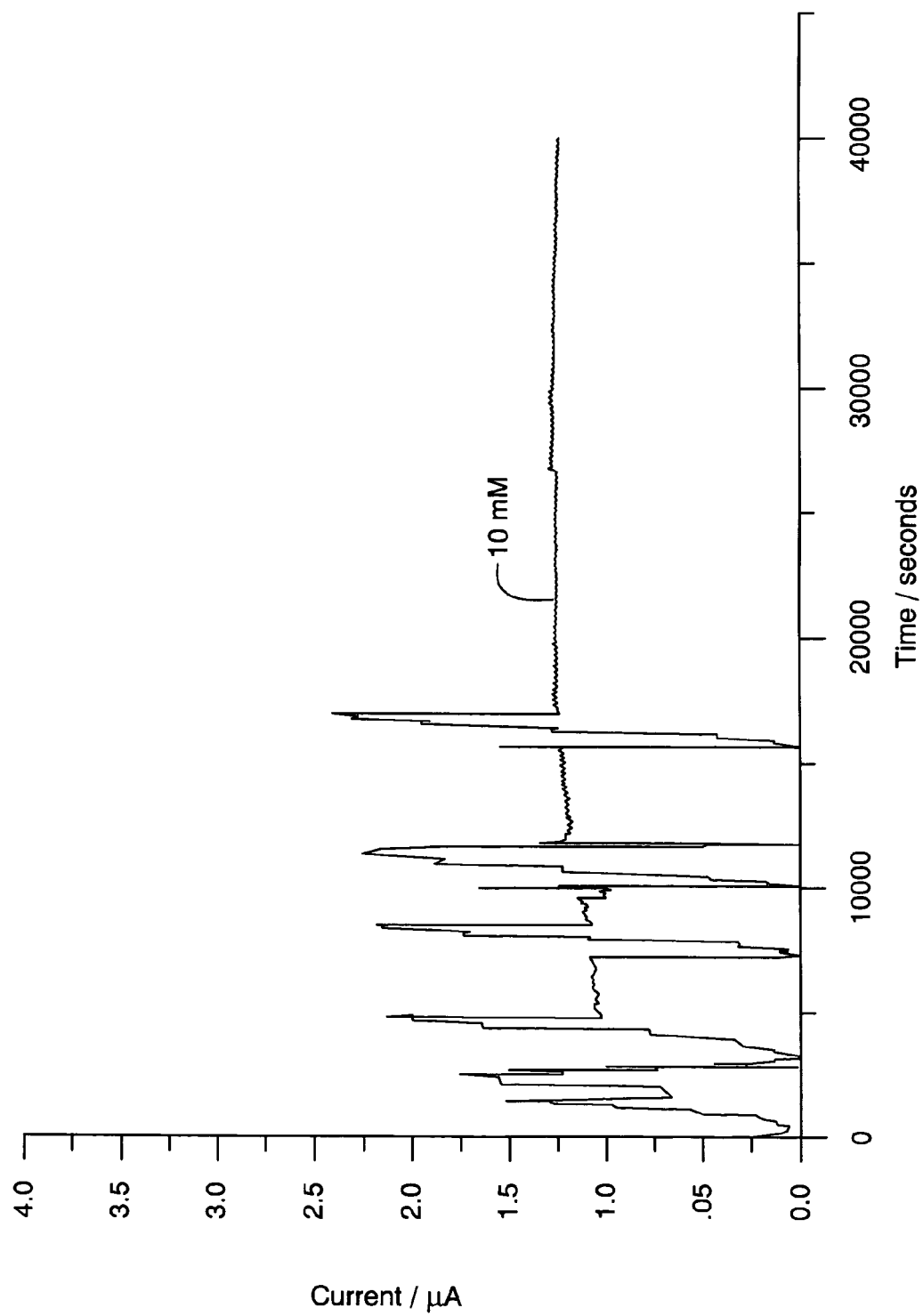
FIG. 8B is a graph depicting current stability over time for an enzymatic electrochemical-based glucose sensor according to an exemplary embodiment of the present invention.

Based on the data of FIGS. 8A and 8B, the enzymatic electrochemical-based sensor of this example is eminently suitable for the detection of physiologically relevant concentrations of glucose, in a continuously operating mode. It was postulated that the water-miscible conductive ink employed in the enzymatic electrochemical-based sensor combined the advantages of an immobilized high molecular weight mediator and immobilized enzyme, with improved electrochemical communication between the enzyme, the mediator and the conductive material.

EXAMPLE 4

A water-miscible conductive ink similar to that of Example 3 was prepared but with the addition of a rheology modifying agent (i.e., Cabosil LM150 hydrophilic fumed silica). The incorporation of a rheology modifying agent (such as Cabosil LM150 hydrophilic fumed silica or Cabosil TS 610 hydrophobic fumed silica) can improve the suitable of the water-miscible conductive ink for screen printing.

The water-miscible conductive ink was formulated by combining 540 mg glucose oxidase from *Aspergillus Niger*, 8.14 g of a 5% aqueous solution of redox polymer 700, 60 g of Coates 66756 water-miscible graphite paste, and 1.6 g Cabosil LM150 hydrophilic fumed silica. The combination was mixed at a high shear rate (i.e., 2000 rpm) for 5 minutes until a uniform, high viscosity paste. The high viscosity paste was then printed through a screen mesh using a DEK 248 screen printer onto an enzymatic electrochemical-based sensor substrate and dried to form a conductive layer. The resulting enzymatic electrochemical-based sensor was essentially as depicted in FIG. 5D.

The enzymatic electrochemical-based structure thus formed was then tested in conjunction with a microfluidic test system. When tested with several glucose concentrations, the response of the enzymatic electrochemical-based structure was largely stable and linear up to 20 mmol glucose concentration at 300 mV, for a period in excess of 10 hours.

Figure 9:
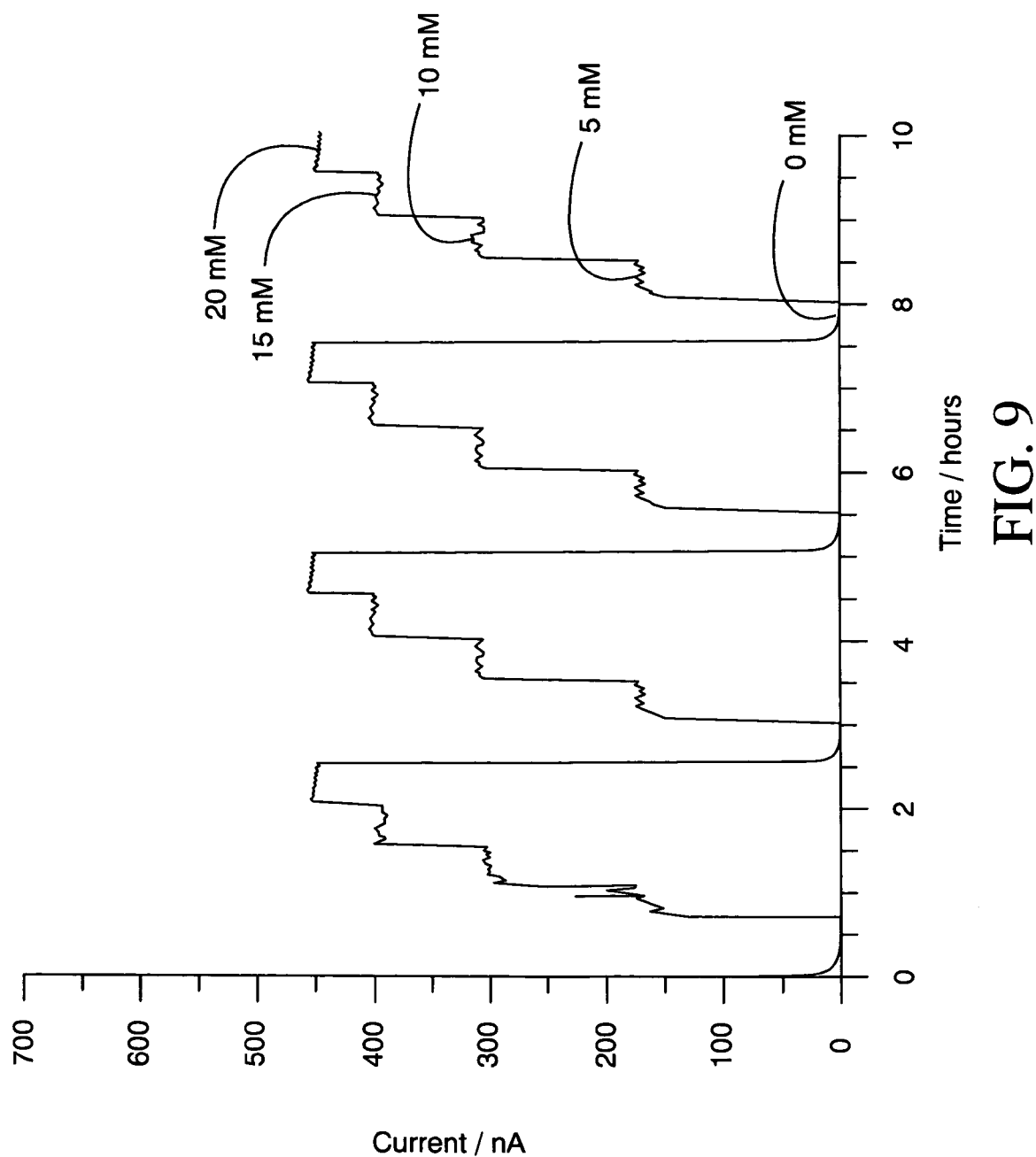
FIG. 9 is a graph depicting calibration data of an enzymatic electrochemical-based sensor according to an exemplary embodiment of the present invention obtained employing a microfluidic test system.

In a further test, various concentrations of glucose in phosphate buffer were flowed through the microfluidic test system at a rate of 200 nL/min. The current response (depicted by the data of FIG. 9) was proportional to glucose concentration employed. The data of FIG. 9 indicates that a continuous stable measurement can be made over a time period in excess of 10 hours, without the need for recalibration or baseline correction.

EXAMPLE 5

A further enzymatic electrochemical-based sensor structure and microfluidic test system as described in Example 4 was prepared and tested with an analyte generated by mixing freshly extracted human plasma with phosphate buffer in a ratio of 1:2 such that the resulting fluid was a close physiological match to human interstitial fluid. Glucose additions were made to this fluid to generate a range of samples that represented the usual physiological glucose range in diabetic persons.

The resulting sample liquid was introduced to the microfluidic test system in 5 minute bursts at a rate of 300 nL/min, during which 0V potential was applied between a working and counter electrode of the enzymatic electrochemical-based sensor structure. This was followed by a 10 minute interval during which the analyte was stagnant. During this 10 minute interval when the analyte was stagnant, a 300 mV potential was applied to the working electrode, and a transient current response was measured. This process was repeated multiple times, each time with the sample liquid containing a different concentration of glucose. The current response generated at each measurement cycle is depicted in FIG. 10.

Figure 10:
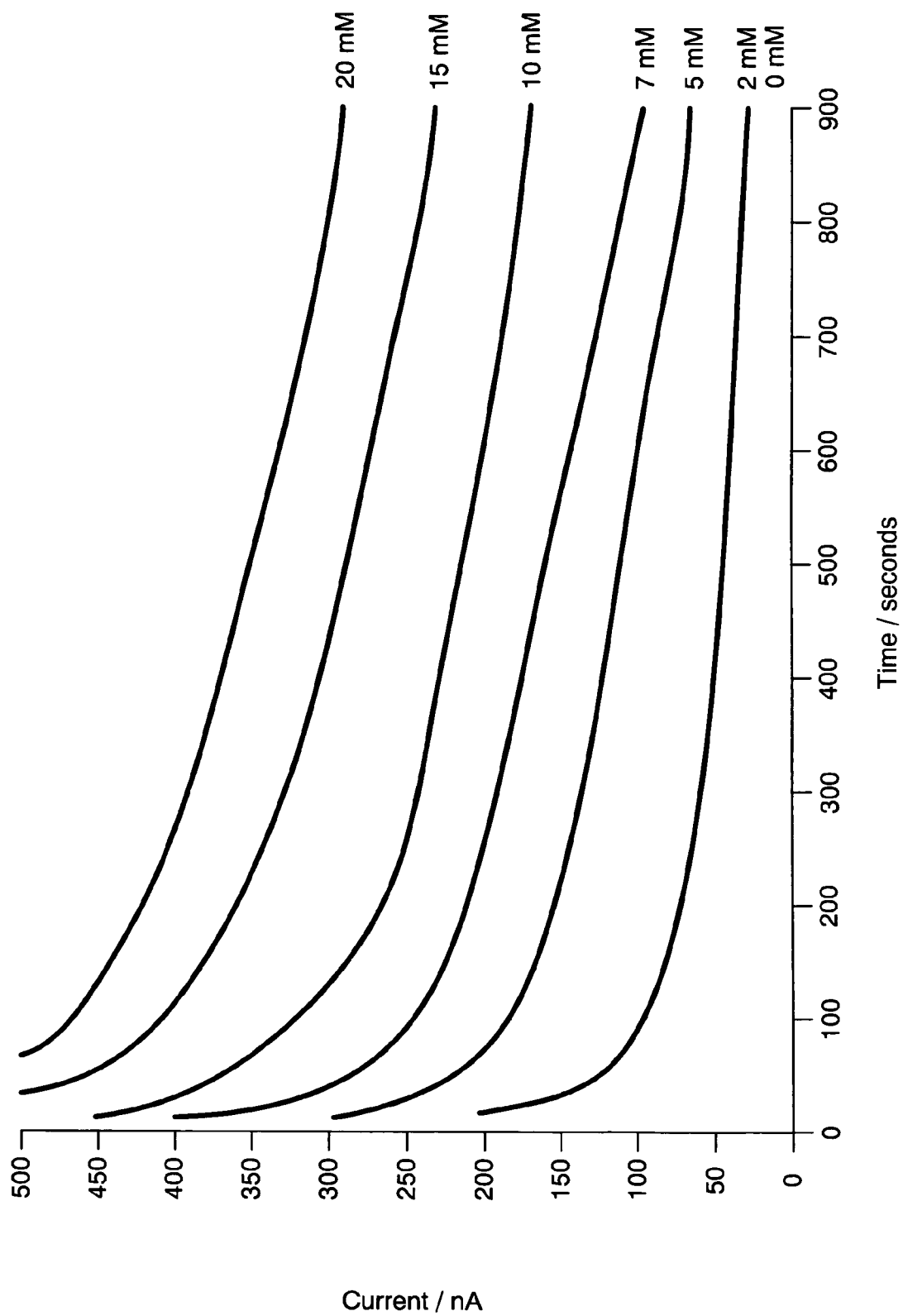
FIG. 10 is a graph depicting transient response to a variety of glucose concentrations for an embodiment of an enzymatic electrochemical-based sensor according to the present invention.
Figure 11:
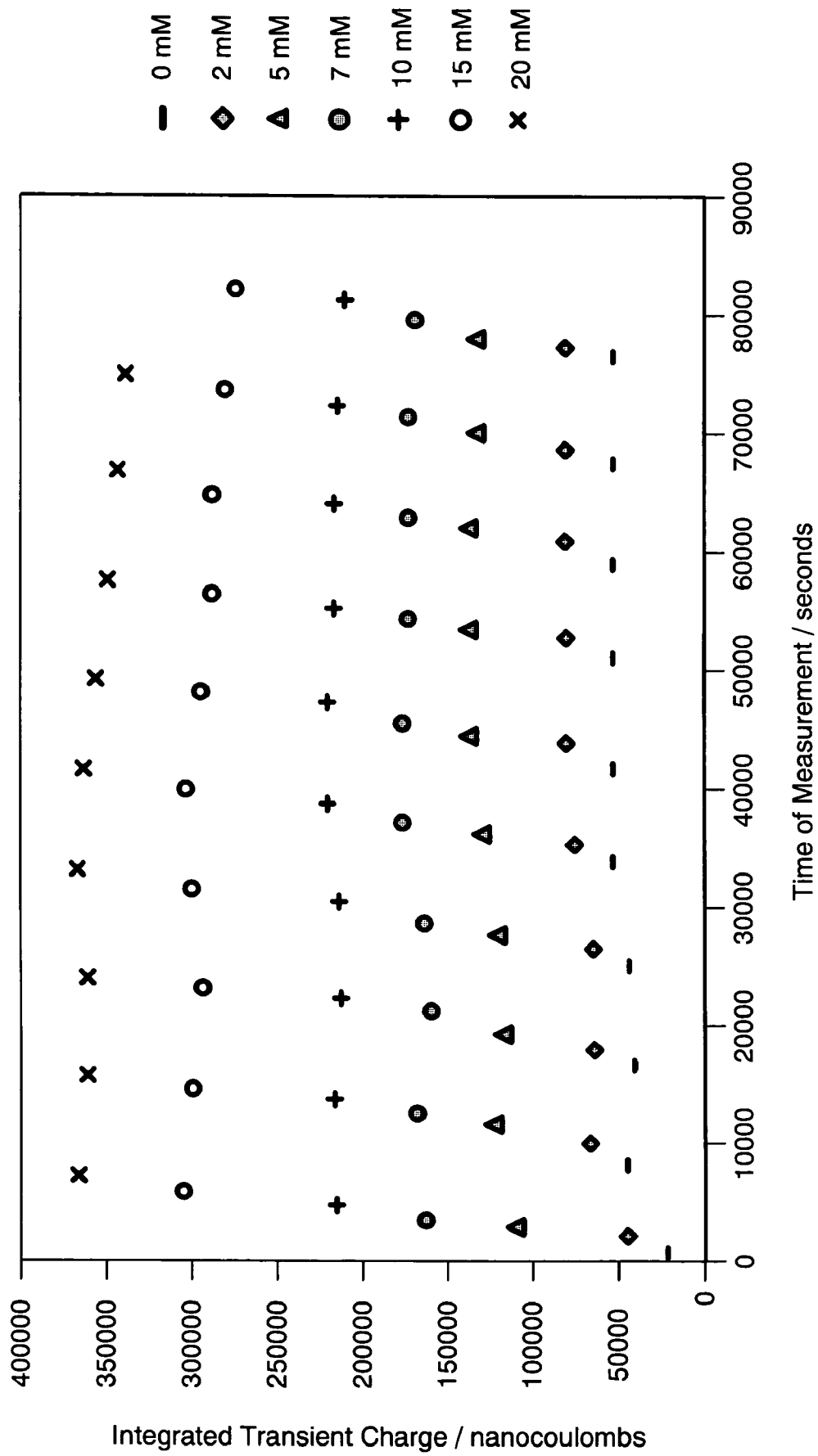
FIG. 11 is a graph depicting integrated transient response to a variety of glucose concentrations for an embodiment of an enzymatic electrochemical-based sensor according to the present invention.
Figure 12:
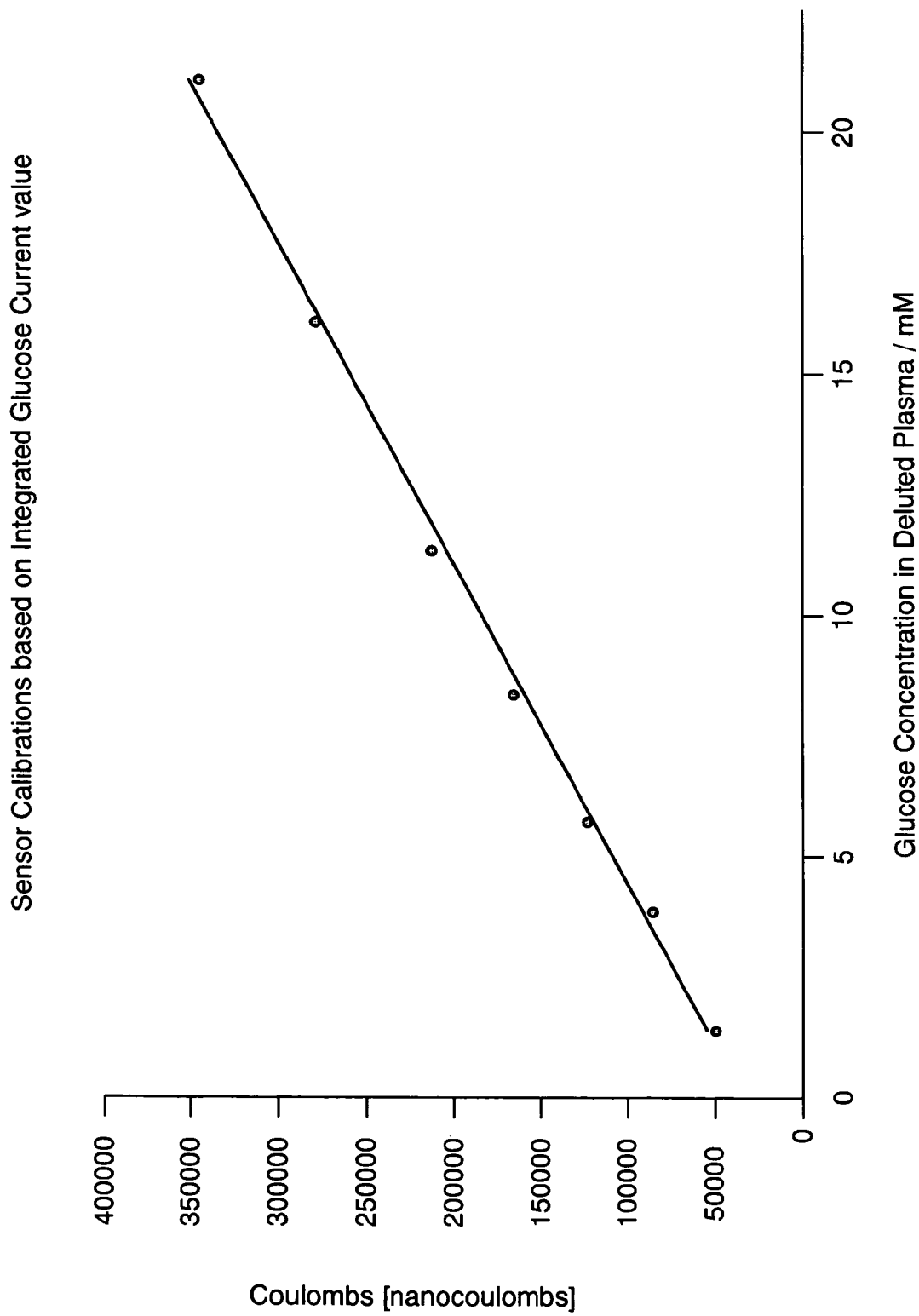
FIG. 12 is a calibration graph for an enzymatic electrochemical-based sensor according to an exemplary embodiment of the present invention.
Figure 13:
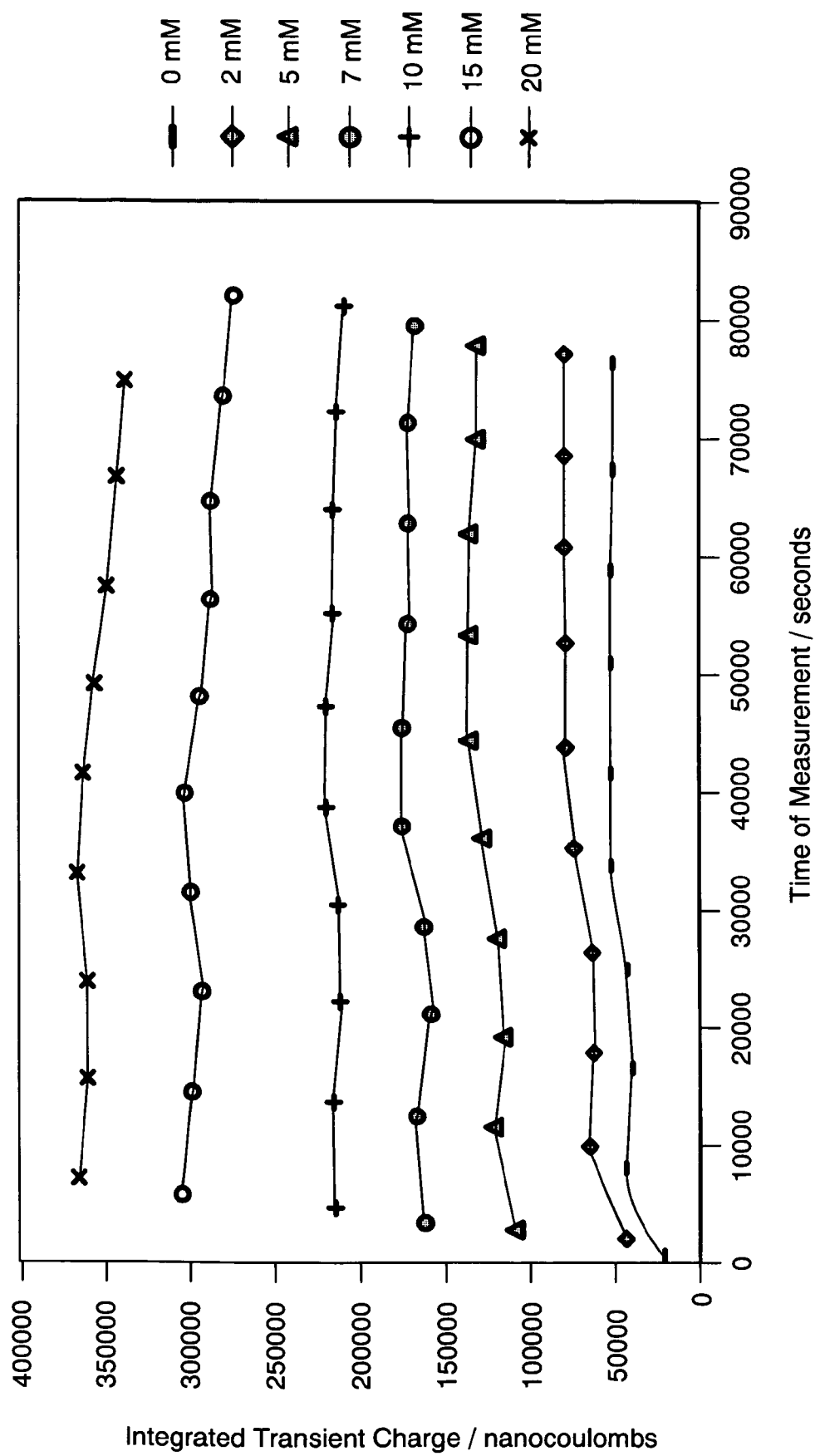
FIG. 13 is a graph depicting response stability for an enzymatic electrochemical-based sensor according to an exemplary embodiment of the present invention.

The data of FIG. 10 represents measurements made at 10-15 minute intervals over a period of time in excess 20 hours. The data of FIG. 10 indicates that glucose concentration can be determined from the current response by either an amperometric measurement of the current at a chosen time or from a coulometric measurement made by taking an integration or partial integration of the current response at a given measurement time. For instance FIG. 11 is a graph representing the coulometric integration of each current transient shown in FIG. 10, indicating both the glucose level of the analyte supplied, and the time at which the measurement was made. FIG. 12 depicts a calibration curve derived from the data of FIG. 11. The data of FIG. 13 indicates that the enzymatic electrochemical-based sensor exhibited stability over a period in excess of 20 hours when tested in the manner described above.

EXAMPLE 6

A water-miscible conductive ink as described in Example 4 and kept refrigerated at 5° C. for 21 days before being tested. When tested as described in Example 4, there was no significant difference between the current response obtained using the water-miscible conductive ink that had been stored for 21 days at 5° C., compared to water-miscible conductive ink that had been manufactured, printed and tested on successive days.

EXAMPLE 7

A water-miscible conductive ink according to en embodiment of the present invention was formulated by mixing 83 g of Precisia LFW201-H water soluble conductive material and binding agent, 8.7 g of a 5% solution of redox polymer 700 (described above), and 0.5 g of Glucose oxidase from *Aspergillus Niger*. After mixing, the resulting water-miscible conductive ink was coated on (i.e., applied to) a printed carbon electrode as described in Example 4. The resulting enzymatic electrochemical-based produced a signal of about 10 nA when exposed to 10 mM glucose. The signal was maintained for the duration of a 1 hour test, thus demonstrating operative immobilization of the various components of the water-miscible conductive ink.

EXAMPLE 8

An water-miscible conductive ink according to the present invention was formulated from 5 g of finely powdered polystyrene-co-maleic anhydride partial iso-octyl ester with a cumene end cap of Mw 2300 (obtained from Aldrich) dissolved in 20 g of 2-butoxyethanol to form a polymeric resin paste. Next, 12 g of graphite powder (particle size 2 micron, obtained from Aldrich) and 2 g of Carbon black (grade black pearls 3700, from Cabot Chemical company) was mixed with the polymeric resin paste on a triple roll mill for 10 minutes. This was followed by a 10 g portion of the resulting mixture being further mixed with 0.5 g of N'N' dimethylethanolamine a volatile counter-ion, available from Aldrich). Next, 3 mls of water was added to form an intermediate mixture. The electrical resistance of a portion of this intermediate mixture coated onto a polyester substrate with a no3 K-bar, was approximately 300 ohms per square.

1.3 grams of the intermediate mixture was mixed with 0.56 g of a 5% aqueous solution of redox polymer 700 and 30 mg of glucose oxidase from *Aspergillus Niger* to create a water-miscible conductive ink according to an embodiment of the present invention.

The water-miscible conductive ink was coated onto a carbon electrode (as depicted in FIGS. 5A through 5D) and tested in a flow system at 0.7 ml per minute with solutions containing glucose at 0.7 ml per minute over a period of about 5 hours. A current of 80 nA in response to a solution of 10 mmol glucose was obtained during the testing.

EXAMPLE 9

A water-miscible conductive ink according to an embodiment of the present invention was formulated by mixing 120 mg of glucose dehydrogenase-PQQ adduct (commercially available from Toyobo, at greater than 500 IU/mg) with 6.1 g of a 3.5% aqueous solution of redox polymer 700. The resulting mixture was added to 65 g of Coates 66756 water-miscible graphite paste. 930 mg of Cabosil LM150 Silica was then added and the resulting composition was mixed with a stirrer at 2000 rpm for 10 minutes.

Figure 14:
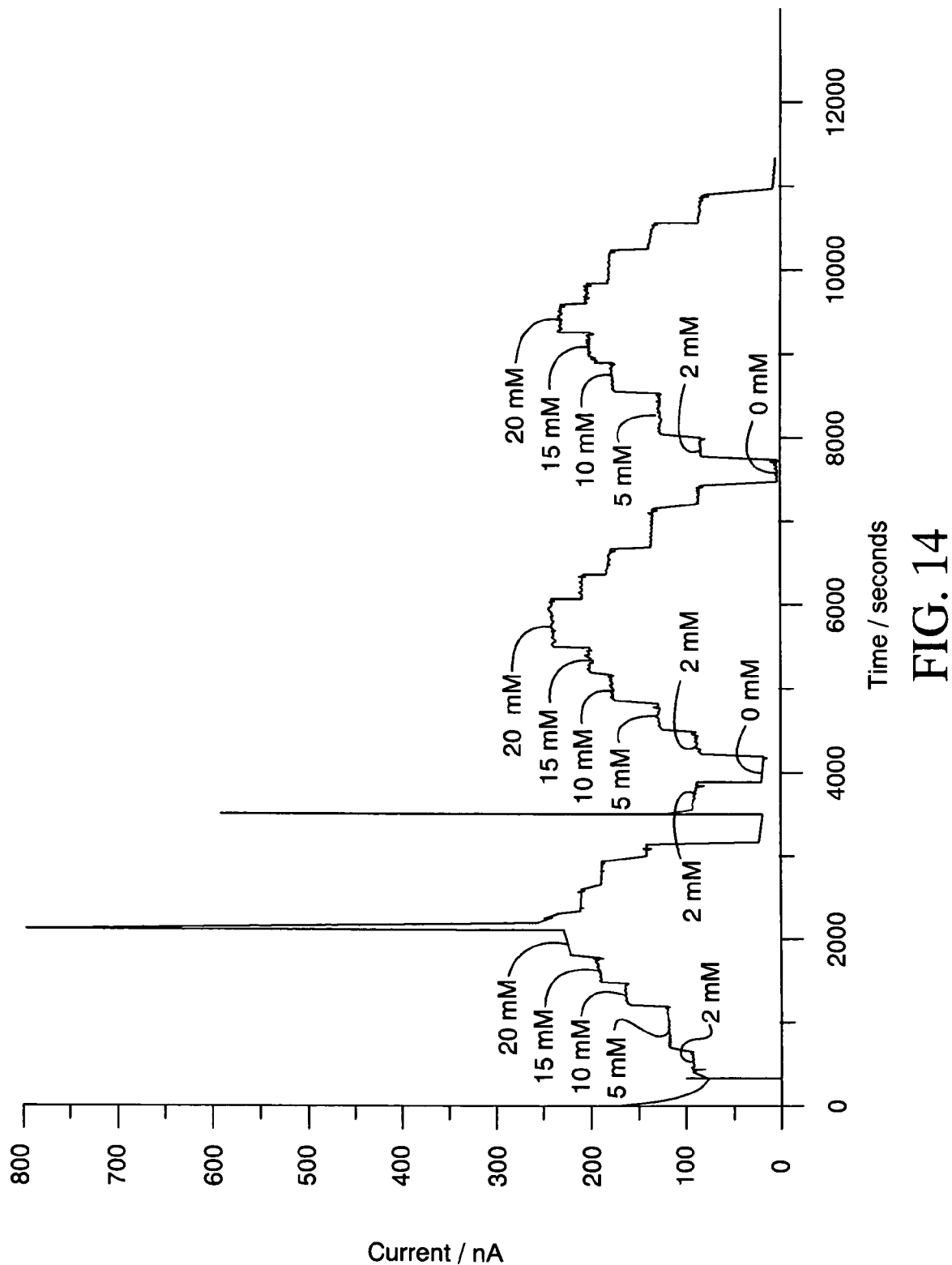
FIG. 14 is a graph depiction calibration data for an enzymatic electrochemical-based glucose sensor according to an exemplary embodiment of the present invention.

The water-miscible conductive ink was printed onto a 3.75 mm$^2$ electrode artwork with a silver/silver chloride reference electrode and dried for 20 minutes at 75° C. to form an enzymatic electrochemical-based sensor. The enzymatic electrochemical-based sensor was tested in a flow-through cell as described in Example 4, at 300 mV applied potential, and using glucose in phosphate buffered saline solution, flowed at 0.7 ml/min. The current response obtained is depicted by the data of FIG. 14. The current response was stable over the 2.5 hours of continuous sensor operation and testing depicted in FIG. 14.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An enzymatic electrochemical-based sensor comprising:
   a substrate; and
   an enzymatic-electrochemically responsive conductive layer formed from a dried water-miscible conductive ink that includes:
   a conductive material;
   an enzyme;
   a mediator; and
   a binding agent,
   wherein the water-miscible conductive ink is formulated as a water-miscible aqueous-based uniform dispersion;
   wherein the binding agent is present as a continuous phase in the water-miscible aqueous-based uniform dispersion and the binding agent became operatively water-insoluble upon drying of the water-miscible conductive ink;
   wherein the binding agent immobilizes the conductive material, mediator and enzyme to the substrate; and
   wherein the immobilization of at least one of the conductive material, mediator and enzyme occurs via ionic binding with the binding agent.

2. The enzymatic electrochemical-based sensor of claim 1, wherein the conductive layer has a conductivity of less than about 10 kΩ.

3. The enzymatic electrochemical-based sensor of claim 1, wherein the conductive layer has a conductivity of less than about 1 kΩ.

4. The enzymatic electrochemical-based sensor of claim 1, wherein the dried binding agent of the enzymatic-electrochemically responsive conductive layer serves as a dialytic membrane.

5. The enzymatic electrochemical-based sensor of claim 1, wherein the substrate is a working electrode.

6. The enzymatic electrochemical-based sensor of claim 1, wherein the mediator is a polymeric mediator.

7. The enzymatic electrochemical-based sensor of claim 1, wherein the enzymatic-electrochemically responsive conductive layer serves as an electrode of the enzymatic electrochemical-based sensor.

8. The enzymatic electrochemical-based sensor of claim 7, wherein the enzymatic-electrochemically responsive conductive layer serves as a working electrode of the enzymatic electrochemical-based sensor.

9. The enzymatic electrochemical-based sensor of claim 1, wherein the enzyme, mediator, and binding agent are essentially uniformly distributed throughout the conductive layer.

\* \* \* \* \*

UNITED STATES PATENT AND TRADEMARK OFFICE
CERTIFICATE OF CORRECTION

PATENT NO. : 7,588,670 B2
APPLICATION NO. : 11/118507
DATED : September 15, 2009
INVENTOR(S) : Rodgers et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 266 days.

Signed and Sealed this

Twenty-first Day of September, 2010

David J. Kappos
*Director of the United States Patent and Trademark Office*